United States Patent [19]

Park et al.

[11] Patent Number: 4,839,014
[45] Date of Patent: Jun. 13, 1989

[54] CLEANER ASSEMBLY, HUMIDIFIER, GAS ALARM AND DETOXIFICATION SYSTEM

[76] Inventors: Sea C. Park; In P. Park, both of 3836 Birchwood, Skokie, Ill. 60076

[21] Appl. No.: 133,924

[22] Filed: Dec. 16, 1987

[51] Int. Cl.⁴ .............................................. C25B 9/00
[52] U.S. Cl. .................................. 204/265; 204/266; 204/431; 55/274; 55/316; 55/259; 261/30; 261/107; 73/23; 340/393; 340/632
[58] Field of Search ............. 204/129, 266, 265, 278, 204/431; 261/30, 107; 55/274, 316, 124, 126, 259; 73/23; 340/623, 393, 634, 635

[56] References Cited

U.S. PATENT DOCUMENTS

| 558,176 | 4/1896 | Huber | 204/278 |
|---|---|---|---|
| 1,581,944 | 4/1926 | Hausmeister | 204/129 |
| 2,771,283 | 11/1956 | Eranosian | 261/30 |
| 3,045,665 | 7/1962 | Moyat | 204/129 |
| 4,141,703 | 2/1979 | Mulchi | 55/316 |
| 4,462,246 | 7/1984 | Advani et al. | 340/632 |
| 4,726,888 | 2/1988 | McCambridge | 204/129 |

FOREIGN PATENT DOCUMENTS 147341 11/1980 Japan .................................. 340/632

Primary Examiner—Bernard Nozick
Attorney, Agent, or Firm—Birch, Stewart, Kolasch & Birch

[57] ABSTRACT

A single assembly of an air processing structure member for air cleaning and humidifying, and an electrochemical reactor which activates a gas alarm for human safety upon detection of a predetermined dosage of gas, such as for example a fatal dose of a gas such as carbon monoxide, and which detoxifies the gas.

6 Claims, 7 Drawing Sheets

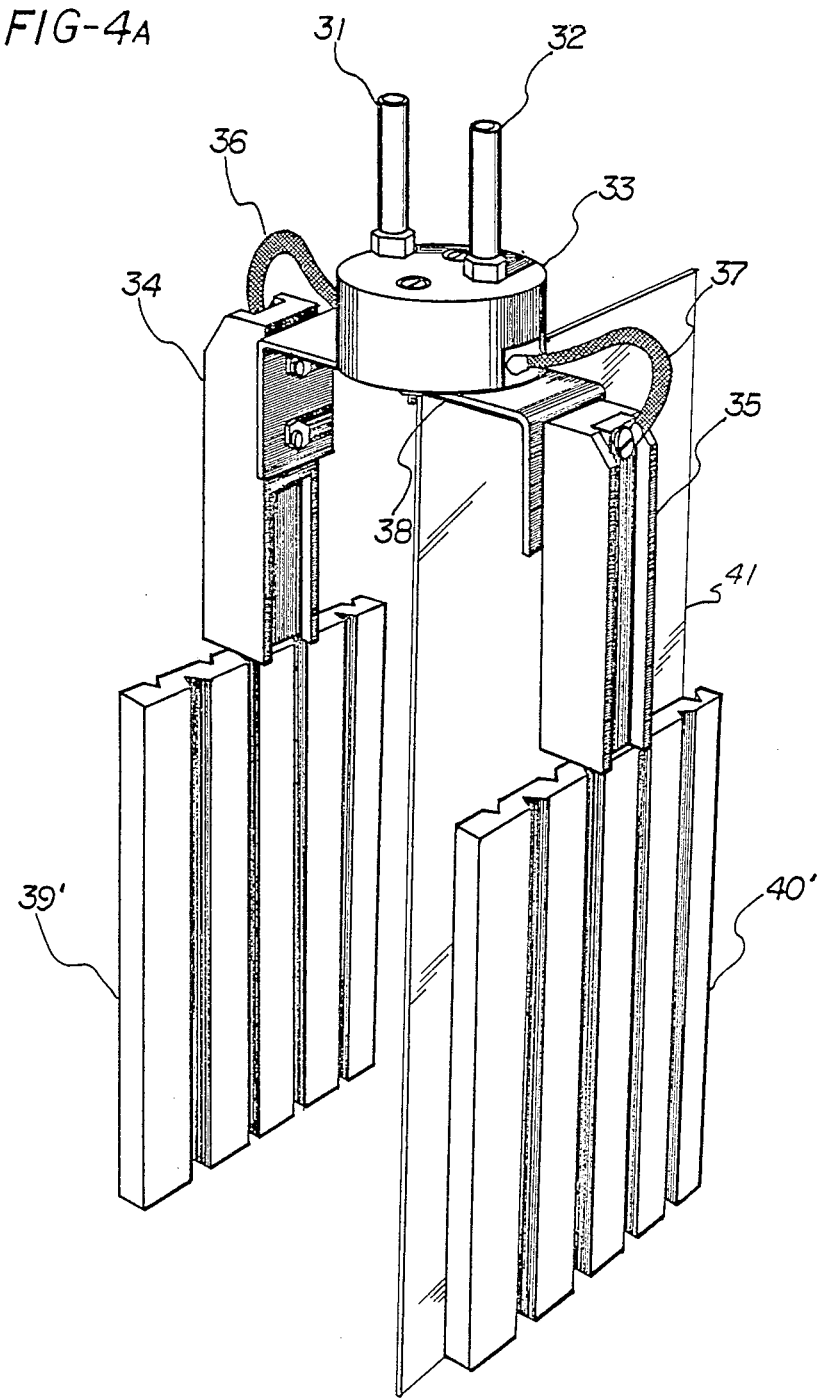

CLEANER ASSEMBLY, HUMIDIFIER, GAS ALARM AND DETOXIFICATION SYSTEM

BACKGROUND OF THE INVENTION

The present invention relates to a multi-functional home appliance air cleaner, humidifier, gas alarm and gas detoxification system. More particularly, the present invention relates to an assembly which includes an air processing structure for air cleaning and humidifying, and an electrochemical reactor which activates a gas alarm for human safety upon detection of a predetermined dosage of gas, such as for example a fatal dose of a gas such as carbon monoxide, and which detoxifies the gas.

Previously, many types of air cleaners, humidifiers, gas alarms and gas detoxification apparatuses have been separately developed. However, these home appliances suffer from a number of difficulties since a separate air cleaner, humidifier, gas-alarm device, and gas detoxification apparatus require separate purchases which are expensive and these devices occupy a large amount of space in a given room.

SUMMARY OF THE INVENTION

Accordingly, it is an object of the present invention to provide a compact home appliance having multiple functions, that is, air cleaning, humidifying, use as a gas alarm, and gas detoxifying for improving human environmental conditions.

Another object of the present invention is to provide a multi-functional appliance which comprises an air processing structure for air cleaning and humidifying, and a electrochemical reactor for activating a gas alarm and gas-detoxifying.

A further object of the present invention is to provide an apparatus which includes in its structure a device for producing and supplying oxygen by the electrolysis of water disposed therein.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to an assembly of an air processing structure for air cleaning and humidifying, and an electrochemical reactor which activates a gas alarm for human safety upon detection of a predetermined gas dosage, such as for example a fatal dose of a gas such as carbon monoxide, and detoxifies the gas.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 4A is a perspective view illustrating another embodiment of the pair of electrodes of the electrochemical reactor of the multi-functional home appliance assembly according to the present invention;

DETAILED DESCRIPTION OF THE INVENTION

Figure 1:
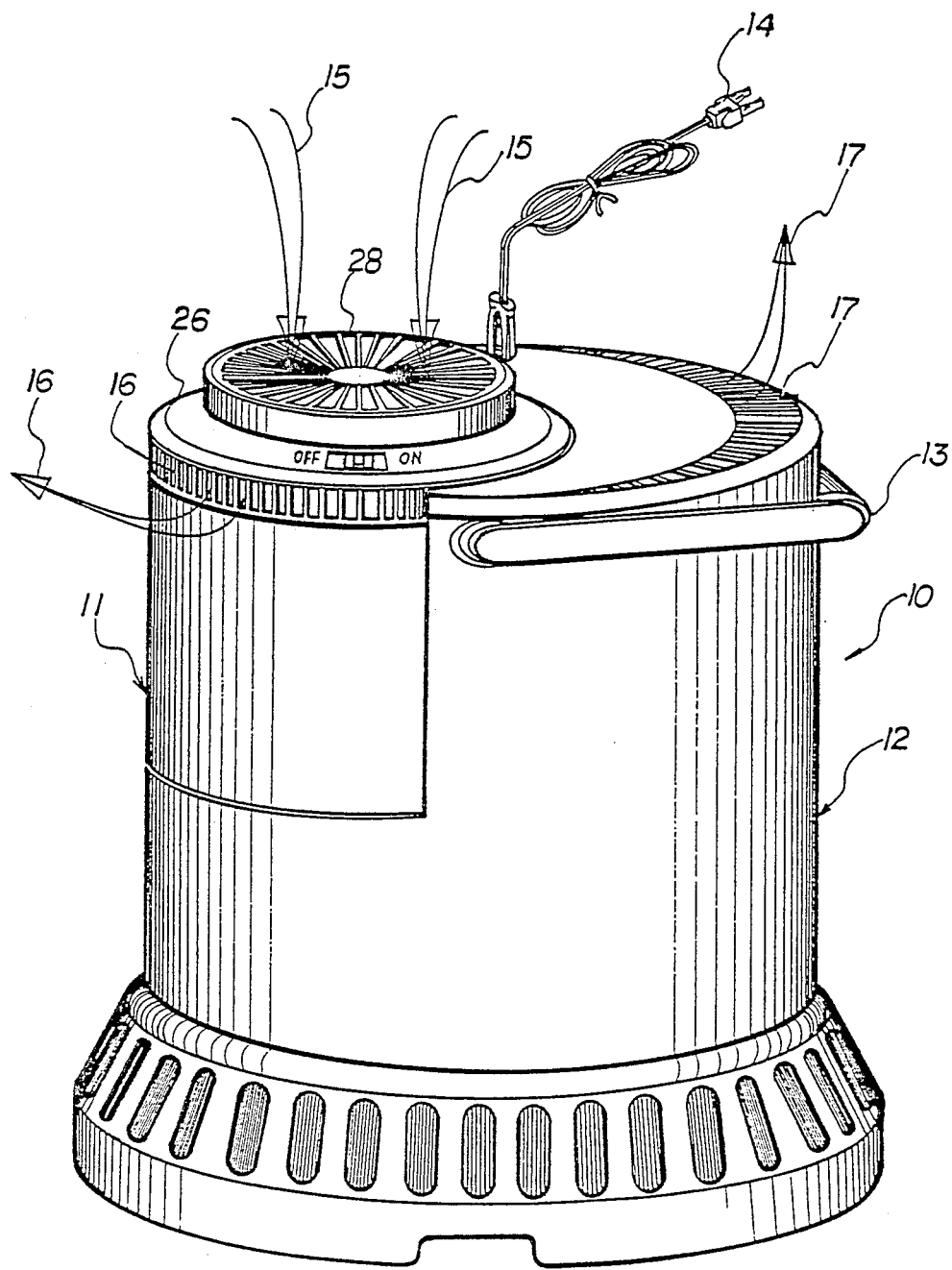
FIG. 1 is a perspective view of a multi-functional home appliance assembly of the present invention.
Figure 2:
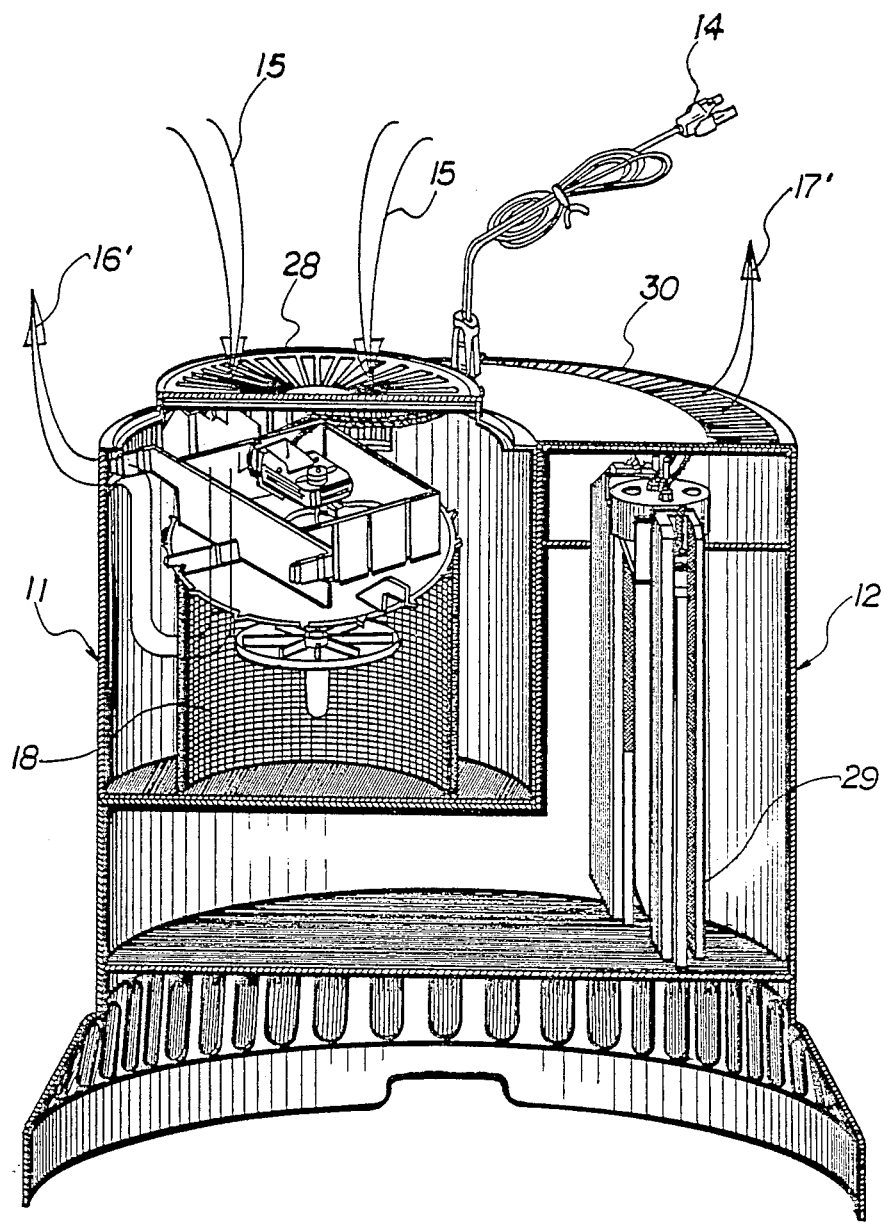
FIG. 2 is a sectional view of FIG. 1.

Referring now in detail to the drawings for the purpose of illustrating preferred embodiments of the present invention, the assembly apparatus 10 as shown in FIGS. 1 and 2 comprises an air processing structure 11 for air-cleaning and humidifying, an electrochemical reactor member 12 for activating a gas alarm and for detoxifying gas and a handle 13.

Figure 3:
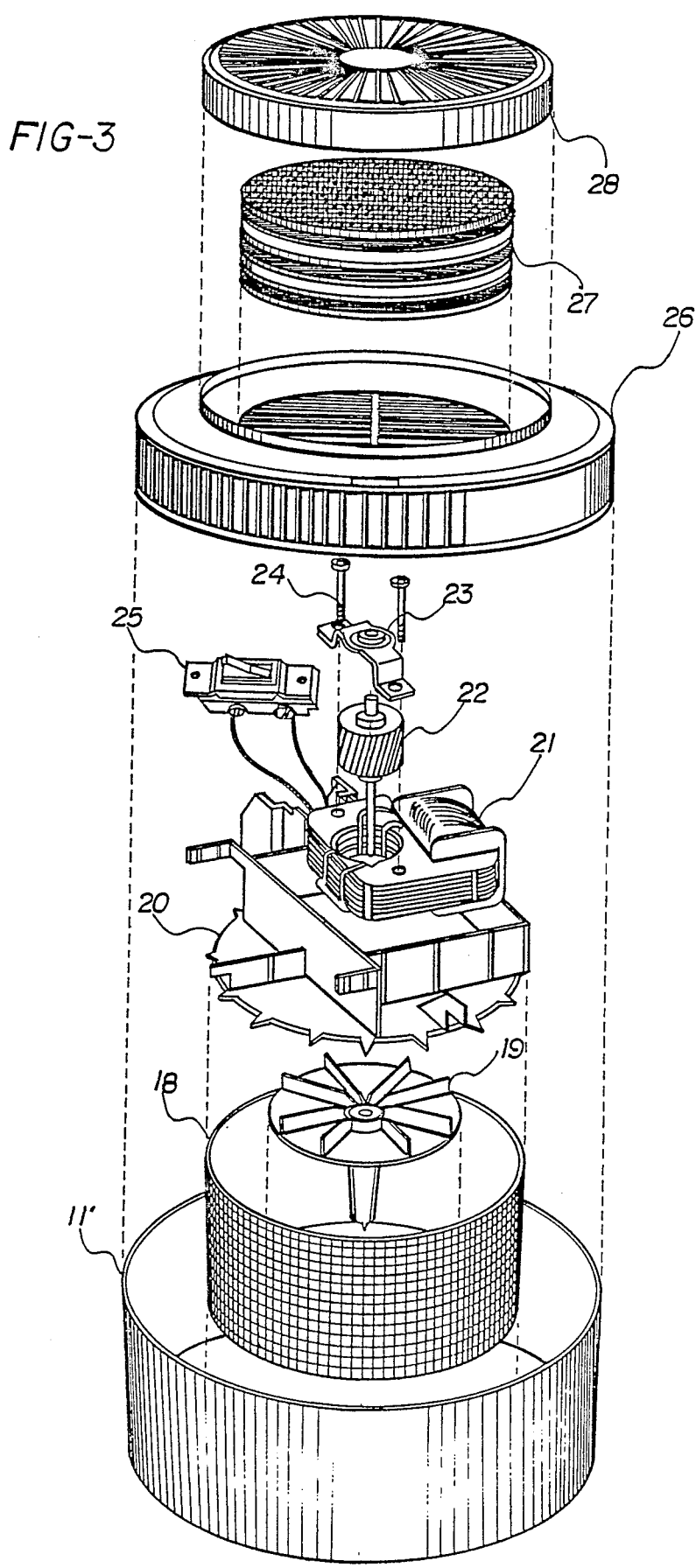
FIG. 3 is an exploded perspective view of a water containing member of the multi-functional home appliance assembly according to the present invention.
Figure 4:
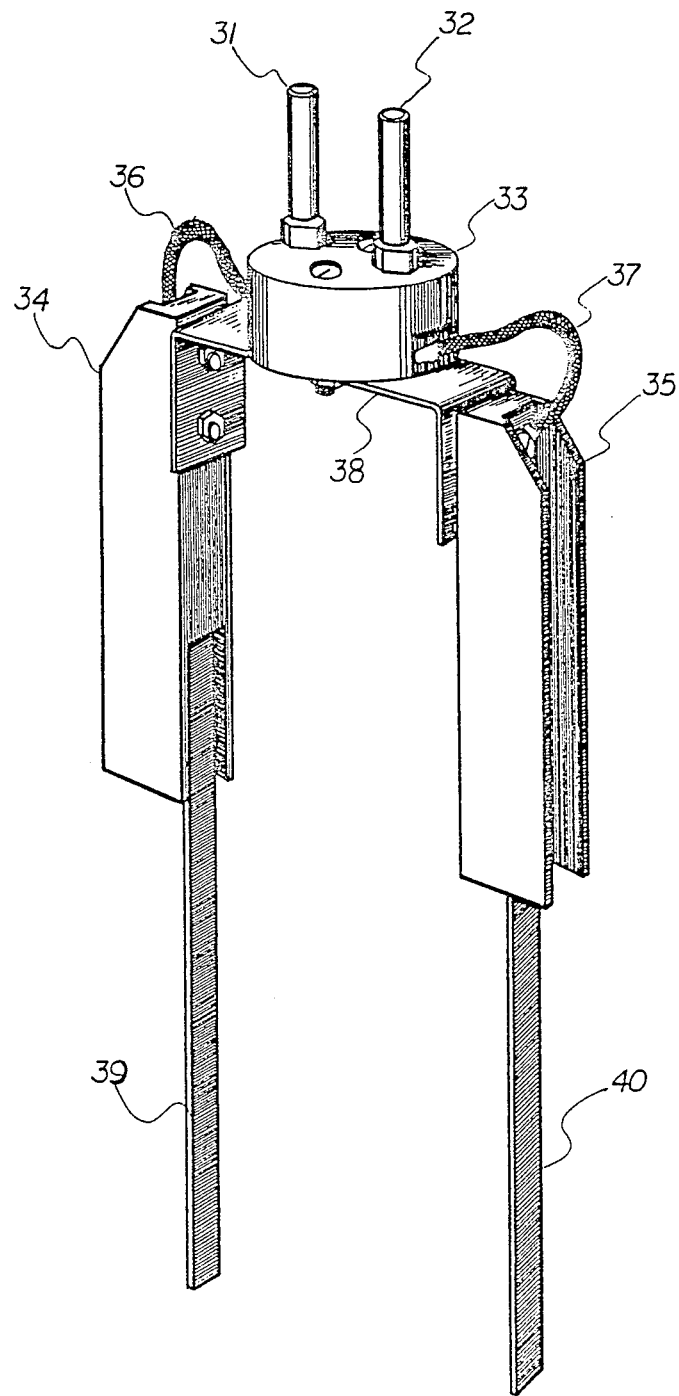
FIG. 4 is a perspective view of a pair of electrodes of a electrochemical reactor of the multi-functional home appliance assembly according to the present invention.
Figure 5:
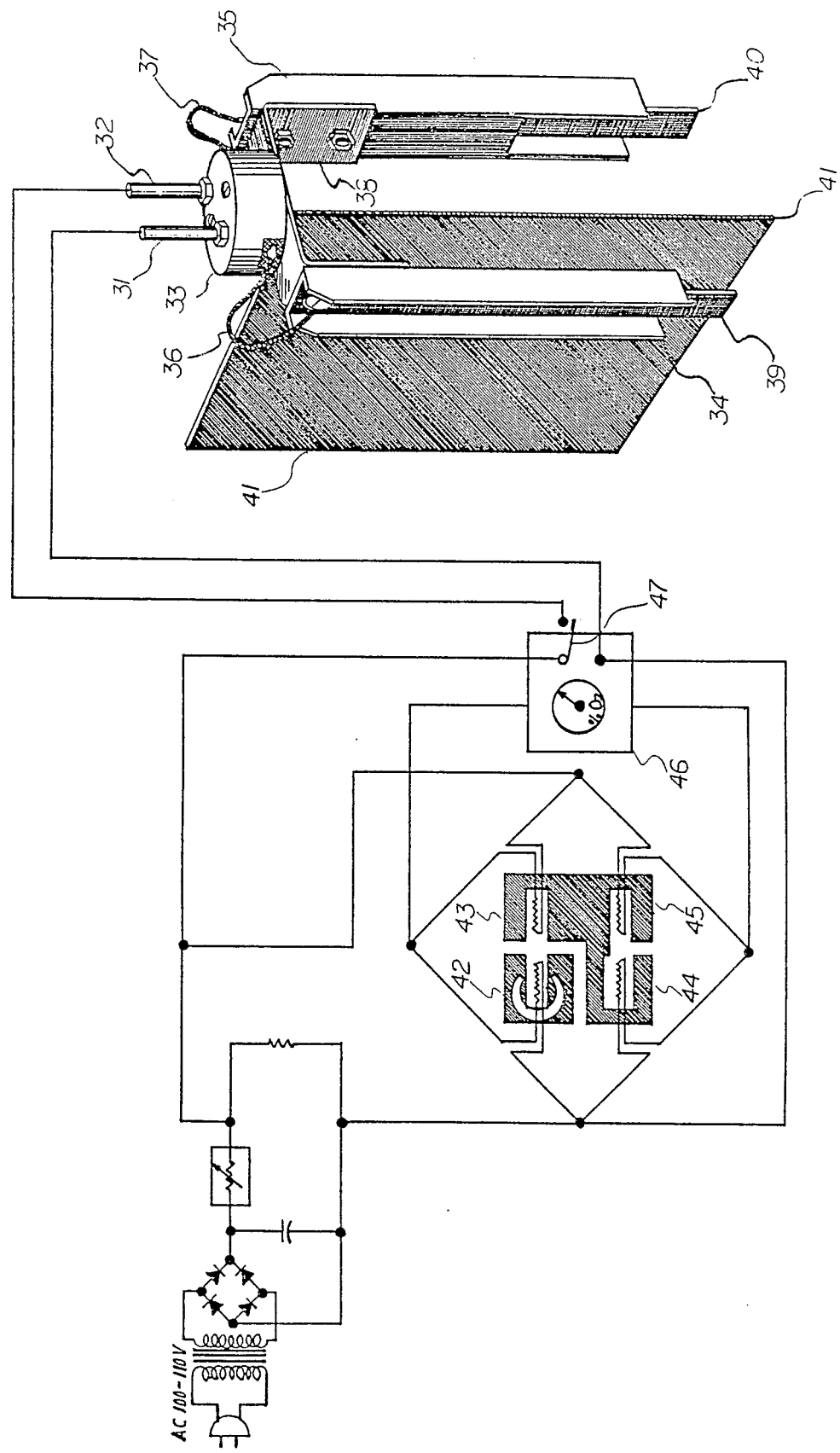
FIG. 5 is a diagrammic view showing a oxygen indicator associated with electrolysis components of the assembly according to the present invention.
Figure 6:
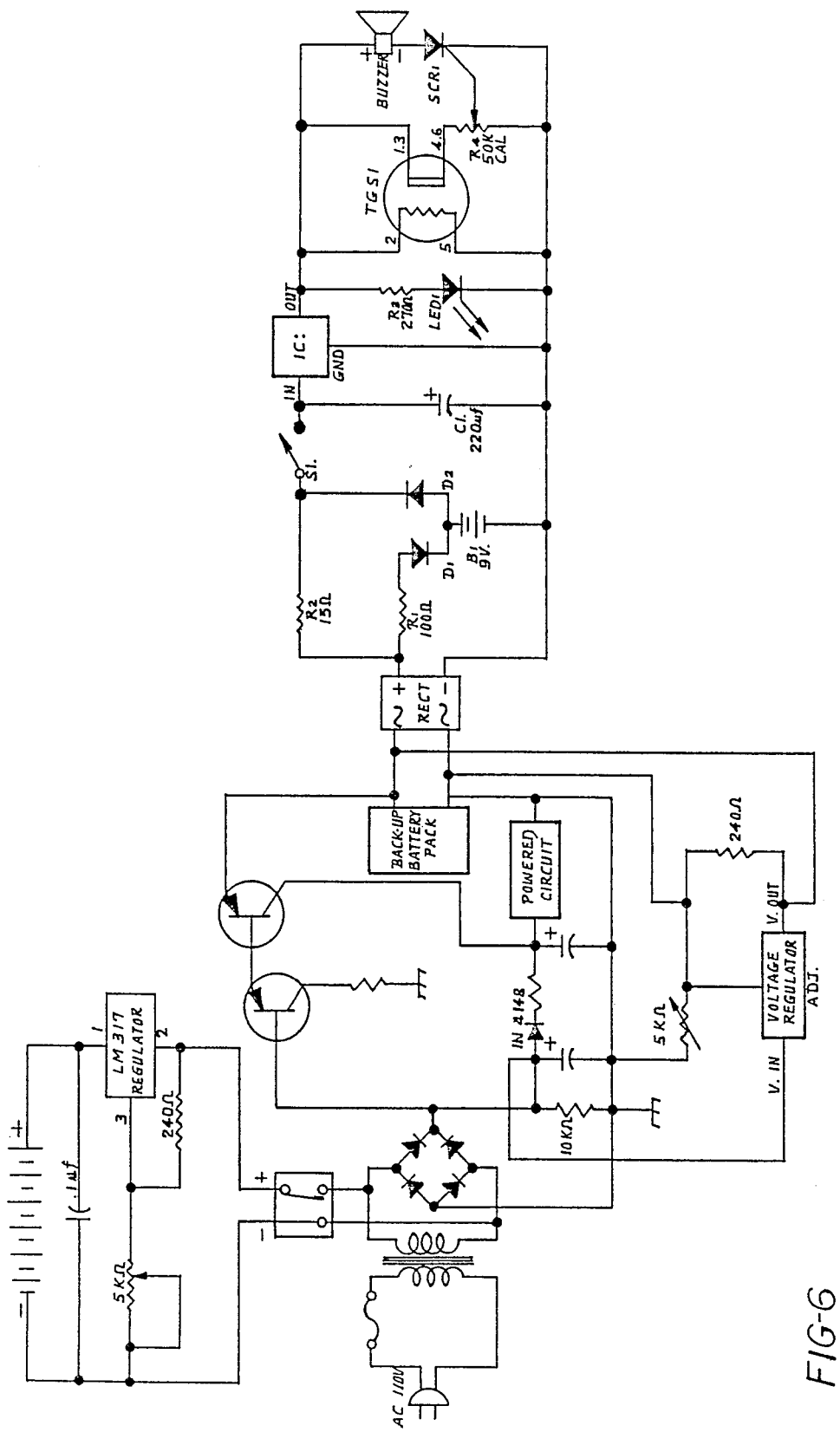
FIG. 6 is a diagrammic view showing an electrical system of an alarm device of the assembly according to the present invention.

As shown in FIG. 3, the air processing structure 11 comprises a water tank 11' containing a water soaked filter chamber 18, an electrical turbo fan 19 disposed within the filter chamber 18, a motor mount housing 20 including a motor rotor 22, a cover 26 containing a plurality of filtering stages 27, and a cover grille 28 for communicating with the atmosphere. The motor mount housing 20 is provided with a motor field winding 21 and an on/off switch 25. Also, the motor rotor 22 is associated with a bearing 23 and screws 24. The plurality of filtering stages 27 for filtering the dirty air such as smoke, dust, pollen, odors etc., includes a first stage containing an impingement fiber for filtering large size airborne particles, a second stage containing a coated fiber for absorbing particles, a third stage containing an activated charcoal filter for absorbing odors, a fourth stage of a woven fabric filter for filtering contaminants, a fifth stage of a coated filter for electrostatically absorbing particles, and a sixth stage of a filter for eliminating submicron airborne pollutants. Therefore, the dirty air 15 in the room is delivered to the bundle of filters 27 for filtering and cleaning the air therethrough. The cleaned air is delivered into the filter chamber 18 by the electrical turbo fan 19 disposed in the filter chamber 18. The cleaned and humidified air 16' is exhausted into the room through a plurality of air outlets 16 disposed at the upper front side portion of the air processing member 11. The air processing structure 11 is detachable from the electrochemical reactor 12. Also, in summer, the air cleaner can be operated individually without water in the water tank 11'. As shown in FIGS. 4, 5 and 6, the electrochemical reactor 12 may be used as a gas alarm, for oxygen-manufacturing, with AC as well as DC current, and with a battery or back up battery pack, and comprises a electrolysis system 29 which includes a cathode 39, an anode 40, an oxygen indicator 46 (FIG. 5), and an electronic circuit (FIG. 6).

The cathode 39 and anode 40 are disposed in ceramic conductive path members 34 and 35, respectively. A frame 38 attached to the ceramic conductive path members 34 and 35 contains a ceramic leading edge 33 disposed thereon. The ceramic leading edge 33 includes a cathode lead 31 connected to a cathode leader cable 36 which is connected to the cathode 39 disposed in the ceramic conductive path member 34, and an anode lead 32 connected to an anode leader cable 37 which is connected to the anode 40 disposed in the ceramic conductive path member 35 (FIG. 4).

Referring in detail to FIG. 4A, there is illustrated an additional embodiment of electrodes of the electrochemical reactor in accordance with the present invention. The electrodes include a large cathode 39' and a large anode 40' for use in a large space area such as an office room, conference room or the like. A diaphragm 41 is disposed between the ceramic conductive path member 34 including the cathode 39 and the ceramic conductive path member 35 including anode 40. The electrolysis system 29 serves to control the supply of oxygen therethrough. That is, a on/off switch 47 is set at a predetermined oxygen percentage for the room and the electrolysis system 29 operates to supply the oxygen. The operation of the electrolysis system 29 is automatically stopped at the predetermined oxygen percentage. As shown in FIG. 5, the oxygen indicator system comprises a sample measuring cell 42, a sample referencing cell 43, and pressure compensating cells 44 and 45 for measuring oxygen in the room. The reaction scheme of the electrolysis to produce oxygen is as follows:

$$2H_2O \rightarrow 2H_2 + O_2$$

$$2H_2O + 2e^- \rightarrow 2H + 2OH^-$$

$$2H \rightarrow H_2 \text{ (Cathode)}$$

$$2OH^- \rightarrow 2OH + 2e^-$$

$$2OH \rightarrow H_2O + \tfrac{1}{2}O_2 \text{ (Anode)}$$

The oxygen 17' from the electrolysis system 29 is exhausted through a plurality of apertures 17 into the room (FIG. 1).

As shown in FIG. 6, the electronic circuit provides for a is provided to transfer from AC to DC by means of a transformer $T_1$. The transformer has 1.2A and 110V/12V. Also, the electronic circuit includes a back up battery pack and a stand-by rechargeable batter. In FIG. 6, $R_1$ represents a 100 OHM and ½W resistor, $R_2$ represents a 15 OHM and 1W resistor, $R_3$ represents a 270 OHM and ½W resistor and $R_4$ represents a 50K OHM and linear potentiometer. $B_1$ represents Ni-Cd cells, $C_1$ is a 220 UF/16V capacitor, $D_1$ and $D_2$ are 1A/200V silicon diodes, and Si is a SPST miniature switch. RECP represents a 50v/1A full wave rectifier, LED represents a red light emitting diode, and 1Cl is a 5 volt regulator. Buzz represents a is piezo electric buzzer, SCRI a 200V/0.8A or 200V/6A silicon-controlled rectifier, and TGSI is gas sensor.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. An appliance assembly for use in a room which comprises:
    an air processing structure for air cleaning and humidifying the room, said air processing structure including a water tank, a filter chamber disposed in said water tank, an electrical turbo fan disposed within said filter chamber, a motor mount housing disposed within said water containing member, a motor rotor supported by said housing operatively associated with said turbo fan, a filter cover containing six filter stages, a cover grille as an air intake disposed on said filter cover for receiving unfiltered air, and a plurality of apertures for exhausting cleaned and humidified air to the atmosphere, wherein said six filter stages include a first stage containing impingement fiber for filtering large size airborne particles, a second stage containing a coated filter for absorbing the particles, a third stage containing an activated charcoal filter for absorbing odors, a fourth stage containing a woven fabric filter for filtering contaminants, a fifth stage containing a coated filter for electrostatically absorbing the particles, and a sixth stage containing a filter for eliminating submicron airborne pollutants; and
    an electrochemical reactor operatively connected to said air processing structure for activating a gas alarm and supplying oxygen to the room, said electrochemical reactor being detachable from said air processing structure, and said electrochemical reactor including an electrolysis system for supplying oxygen, an oxygen controlling system for controlling the supply of oxygen at a predetermined percentage in the room and a gas alarm system for monitoring carbon monoxide,
    wherein the assembly is constructed so as to be used as an air cleaner, humidifier, gas alarm, and oxygen-supplier.

2. The assembly of claim 1, wherein the gas alarm system includes an on/off switch operatively associated therewith, a buzzer operatively connected to said switch, cells, plurality of resisters, and diodes operatively associated with said buzzer for activating said buzzer upon detecting the presence of said carbon monoxide.

3. The assembly of claim 1, wherein the electrolysis system contains a first ceramic conductive path member which includes a cathode, a second ceramic conductive path member which includes an anode, and a diaphragm operatively disposed between said first and second ceramic conductive path members.

4. The assembly of claim 3, wherein the oxygen controlling system includes an on/off switch operatively associated therewith, and an oxygen percentage meter operatively connected to a sample measuring cell, a sample referencing cell, and a pressure compensating cells for measuring oxygen in the room.

5. The assembly of claim 3, wherein the cathode disposed in the ceramic conductive path member is operatively connected to a cathode lead through a cathode leader cable.

6. The assembly of claim 5, wherein the anode disposed in the ceramic conductive path member is operatively connected to an anode lead through an anode leader cable.

* * * * *